(12) United States Patent
Releford

(10) Patent No.: US 12,322,109 B2
(45) Date of Patent: Jun. 3, 2025

(54) METHODS AND SYSTEMS FOR IMPROVING WOUND HEALING

(71) Applicant: Wound Pros Technology, Inc., Los Angeles, CA (US)

(72) Inventor: Bill J. Releford, Los Angeles, CA (US)

(73) Assignee: Wound Pros Technology, Inc., Los Angeles, CA (US)

( * ) Notice: Subject to any disclaimer, the term of this patent is extended or adjusted under 35 U.S.C. 154(b) by 91 days.

(21) Appl. No.: 18/749,457

(22) Filed: Jun. 20, 2024

(65) Prior Publication Data

US 2024/0428416 A1  Dec. 26, 2024

Related U.S. Application Data

(60) Provisional application No. 63/596,381, filed on Nov. 6, 2023, provisional application No. 63/522,515, filed on Jun. 22, 2023.

(51) Int. Cl.
| | | |
|---|---|---|
| G06T 7/00 | (2017.01) | |
| G06T 7/11 | (2017.01) | |
| G06T 7/62 | (2017.01) | |
| G16H 15/00 | (2018.01) | |
| G16H 20/10 | (2018.01) | |

(52) U.S. Cl.
CPC .............. *G06T 7/0016* (2013.01); *G06T 7/11* (2017.01); *G06T 7/62* (2017.01); *G16H 15/00* (2018.01); *G16H 20/10* (2018.01); *G06T 2207/10004* (2013.01); *G06T 2207/20081* (2013.01); *G06T 2207/20084* (2013.01); *G06T 2207/30088* (2013.01)

(58) Field of Classification Search
CPC . G06T 7/0016; G06T 7/11; G06T 7/62; G06T 2207/10004; G06T 2207/20081; G06T 2207/20084; G06T 2207/30088; G16H 15/00; G16H 20/10
See application file for complete search history.

(56) References Cited

U.S. PATENT DOCUMENTS

| | | | |
|---|---|---|---|
| 11,850,025 B2 * | 12/2023 | Fright | A61B 5/445 |
| 11,903,723 B2 * | 2/2024 | Barclay | A61B 5/7475 |
| 2006/0116904 A1 * | 6/2006 | Brem | G16H 15/00 |
| | | | 705/2 |

(Continued)

FOREIGN PATENT DOCUMENTS

| | | |
|---|---|---|
| KR | 1020210002184 A | 1/2021 |
| WO | 2018160963 A1 | 9/2018 |

OTHER PUBLICATIONS

Ananian, C. "Wound Closure Outcomes Suggest Clinical Equivalency Between Lyopreserved and Cryopreserved Placental Membranes Containing Viable Cells" Advances in Wound Care, vol. 8, Issue 11, pp. 523-605 (Year: 2019).*

(Continued)

*Primary Examiner* — Mia M Thomas
(74) *Attorney, Agent, or Firm* — Fox Rothschild LLP

(57) ABSTRACT

This disclosure provides a novel method and system for wound assessment and treatment to improve wound healing. The disclosed method and system employs machine learning models to extract information from collected wound images and other data to determine wound healing rates and appropriate treatment plans.

19 Claims, 5 Drawing Sheets

(56) References Cited

U.S. PATENT DOCUMENTS

| | | | | |
|---|---|---|---|---|
| 2013/0149368 | A1* | 6/2013 | Yu | A61L 15/28 |
| | | | | 424/445 |
| 2016/0284084 | A1* | 9/2016 | Gurcan | G16H 30/40 |
| 2017/0236281 | A1* | 8/2017 | Dacosta | G06T 7/0016 |
| | | | | 382/128 |
| 2020/0193597 | A1* | 6/2020 | Fan | H04N 25/135 |
| 2020/0268808 | A1* | 8/2020 | Wang | A61P 17/02 |
| 2021/0290152 | A1* | 9/2021 | Vogel | G16H 40/67 |
| 2021/0386295 | A1* | 12/2021 | Dickie | A61B 5/6898 |
| 2022/0292677 | A1* | 9/2022 | Pesala | G06T 7/0012 |

OTHER PUBLICATIONS

Jessup, Rebecca L. MPH, BPod. What is the Best Method for Assessing the Rate of Wound Healing?: A Comparison of 3 Mathematical Formulas. Advances in Skin & Wound Care 19(3):p. 138-147, Apr. 2006. (Year: 2006).*

Xu, Y. "Personalized prediction of chronic wound healing: An exponential mixed effect model using stereophotogrammetric measurement" Journal of Tissue Viability (2014) 23, pp. 48-59 (Year: 2014).*

Robnik-Sikonja, M. et al. "Evaluation of Prognostic Factors and Prediction of Chronic Wound Healing Rate by Machine Learning Tools" S. Quaglini, P. Barahona, and S. Andreassen (Eds.): AIME 2001, LNAI 2101, pp. 77-87, 2001 (Year: 2001).*

John J. Squiers, MD, et al., Machine learning analysis of multispectral imaging and clinical risk factors to predict amputation wound healing, Journal of Vascular Surgery, vol. 75, Issue 1, Jan. 2022, pp. 279-285.

International Search Report and Written Opinion issued on Oct. 11, 2024 for International Patent Application No. PCT/US2024/034884 (11 pages).

* cited by examiner

WOUND TRACK

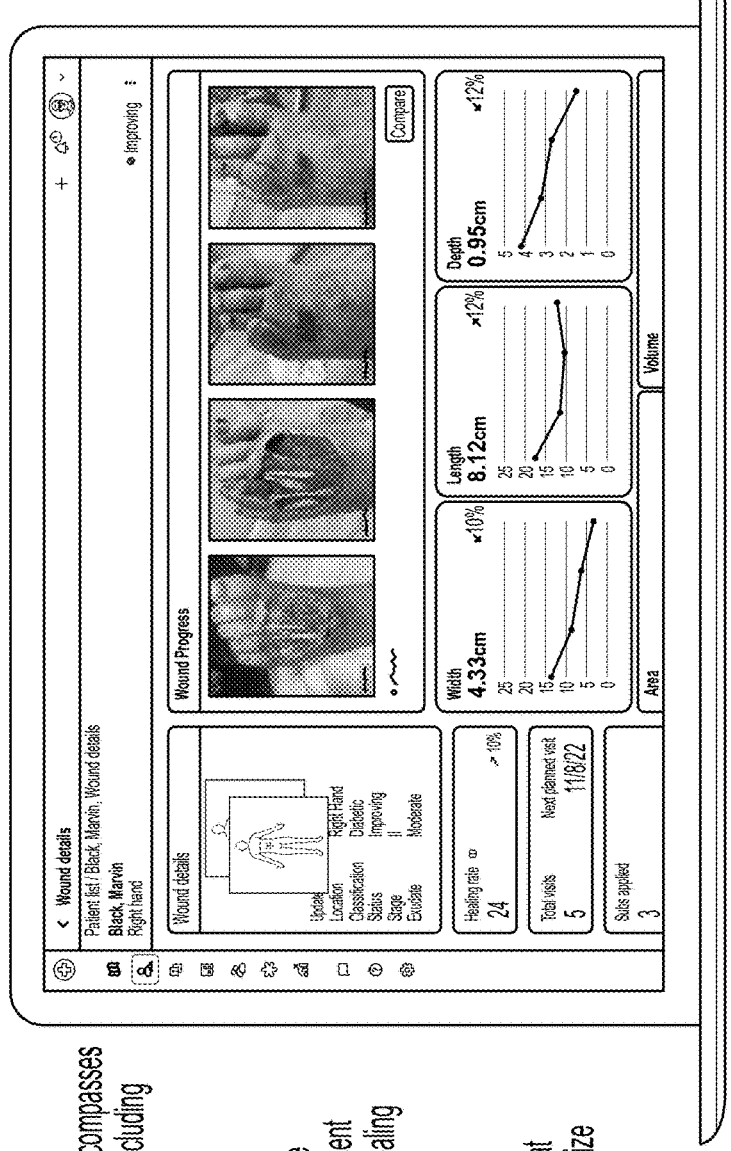

Four Week Progress
The Wound Pros Progress Report encompasses four weeks of data for each wound, including pictures and measurements

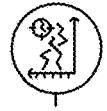

Healing Rate
Our progress report predicts when the wound will close, based on the treatment protocols we are using, and recent healing progression

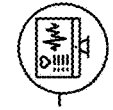

Visual Trends
Our progress report shows graphs that display various trends related to the size of the wound being treated

Fig. 1

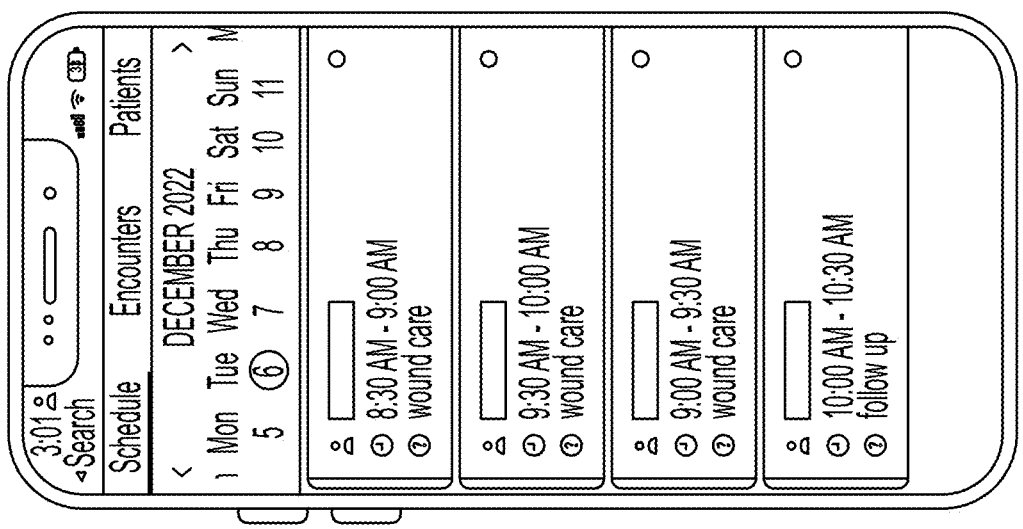

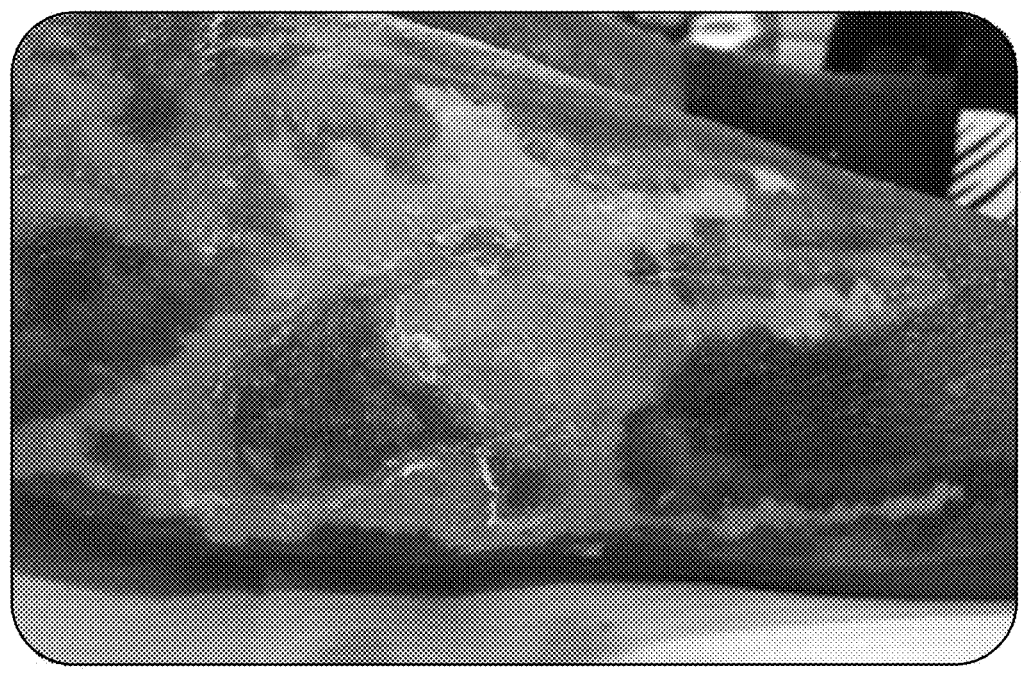

Patient Referral
Medicare, Medicare/Medicaid Dual

Visit Scheduled
A wound evaluation is scheduled with one of our wound care consultants.

Wound Evaluation
Wounds are evaluated at bedside or via telemedicine considering the current pandemic.

Treatment Plan Created
Using our comprehensive treatment protocol, a treatment plan is created for each wound.

Report Generation
Within 48 hours, a detailed treatment report is generated and available via our secure HIPAA-compliant facility portal.

Fig. 3

METHODS AND SYSTEMS FOR IMPROVING WOUND HEALING

CROSS-REFERENCE TO RELATED APPLICATIONS

This application claims priority under 35 U.S.C. § 119(e) to U.S. Provisional Patent Application No. 63/522,515, filed Jun. 22, 2023, and U.S. Provisional Patent Application No. 63/596,381, filed Nov. 6, 2023. The foregoing applications are incorporated by reference herein in their entireties.

FIELD

The present invention relates generally to methods and systems for determining a healing rate of a wound or a portion thereof on a subject to improve wound healing.

BACKGROUND

Chronic and complex wounds, including venous, diabetic, and pressure ulcers, surgical wounds, ostomy, and other complex wounds, affect millions of patients in the United States alone. Billions of dollars are spent on the treatment of chronic wounds in the United States annually, including billions on wound care products. The cost of treating chronic wounds continues to grow year after year due to an aging population and rising incidence of diabetes and obesity. The treatment cost for chronic wounds has become a significant financial burden to the individual and society.

People suffer from chronic and compromised wounds with debilitating pain and reduced quality of life for those whose health is already compromised. Patients with this condition often present to a doctor at late stages of the disease, which leads to many amputations, which may be avoidable. Moreover, proper diagnostics requires specialized vascular labs, which precludes these types of tests from being performed outside major hospitals and in an expedited fashion.

While advances in medical technology have helped bring new treatment modalities to the various wound types, there is a large unmet need for accurate and objective assessment of a wound and the wound healing progress. Objective assessment of wound healing progress is the basis for determining the effectiveness of a treatment pathway, and is critical in selecting the best treatment plan. Objective assessment includes comparative analysis. With standardized measurements, healthcare professionals can accurately compare the progression of wounds over time. Variabilities in methods can lead to inconsistencies and misinterpretations. It also involves determining treatment efficacy. Evaluating the effectiveness of treatments becomes more straightforward. If measurements are consistent, changes (improvements or deteriorations) are more reliably attributed to the treatment itself. Other factors of objective assessment include data recording and communication, research and development, patient outcomes and safety, regulatory compliance, and cost efficiency. Data recording and communication includes Electronic Health Records (EHRs); standard measurements streamline data entry into EHRs, ensuring that the data is uniform and usable across different platforms and systems. It also includes interdisciplinary communication; nurses, doctors, and specialists often need to collaborate. Standardized measurements ensure everyone is on the same page, fostering clear and effective communication. Research and development includes clinical trials and innovation. Standardization is crucial for clinical trials, where data integrity is paramount. It ensures that results from different studies can be compared, aggregated, and analyzed comprehensively. For innovation, reliable data enables better R&D, paving the way for new treatments and technologies. Patient outcomes and safety include improved care plans; with clear and consistent wound measurements, healthcare providers can design more effective and personalized care plans. It also includes risk management; identifying at-risk wounds (that may not heal properly) becomes easier, allowing for timely interventions and reducing complications. Regulatory compliance includes guidelines and standards; regulatory bodies often require adherence to specific standards. Following these guidelines and standards helps in maintaining compliance and avoiding legal complications. It also includes quality control; standardized practices improve the overall quality of care, adhering to best practices and ensuring patient safety. Finally, cost efficiency includes resource management and reduced errors. Accurate measurements mean better resource allocation. Supplies, staff time, and medical interventions can be managed more efficiently.

Decision-making by healthcare providers during the wound evaluation process may be challenging and difficult due to the lack of quantitative criteria which can facilitate an accurate assessment of the quality of the wound progression or healing trends. Few mathematical models in the literature deal with the complexities associated with wound healing. Existing methods for assessment of wound status in terms of time are often based on measurements of wound area and, to a lesser extent, of the wound perimeter, and the linear healing rate (D) has been often utilized. However, the use of these methods has been limited by their low precision of assessment. Implications of inaccurate wound measurements include financial implications, legal implications, and clinical implications. For example, financial implications include increased healthcare costs; inaccurate measurements may lead to improper treatment plans, which can result in prolonged hospital stays and more frequent doctor visits, driving up costs. Financial implications also include wasted resources; resources might be allocated incorrectly, leading to misuse or overuse of medical supplies and medications. Financial implications additionally include reimbursement issues; payers, including insurance companies and Medicare, often rely on accurate reporting for reimbursement. Inaccuracies could lead to denied claims or reduced reimbursements. Legal implications include medical malpractice; incorrect wound measurements can lead to inappropriate treatments, which might harm patients and result in legal actions against healthcare providers. Legal implications also include regulatory Compliance: Healthcare providers must comply with various regulations that often require precise documentation. Inaccurate measurements can lead to noncompliance and potential penalties. Legal implications additionally include liability; the healthcare facility might face liability issues if patients suffer due to incorrect wound care, leading to potential lawsuits and loss of reputation. Clinical implications include impeded healing progression; improper measurements can lead to inadequate or excessive treatments, either of which could slow down or complicate the healing process. Clinical implications also include incorrect monitoring: it becomes challenging to monitor wound progress accurately, leading to potential underestimation or overestimation of healing stages. Clinical implications additionally include complications; inaccurate assessments can miss early signs of complications such as infections, leading to potentially serious health outcomes for the patient.

Thus, there remains a pressing need for improved methods to standardize the manner in which chronic wounds are analyzed accurately and consistently with the ultimate goal to improve wound healing outcomes.

SUMMARY

This disclosure addresses the need mentioned above in a number of aspects. In one aspect, this disclosure presents a method for determining a wound healing rate of a wound or a portion thereof on a subject. In some embodiments, the method comprises: (a) obtaining image data comprising an image of a wound or a portion thereof of a subject; (b) automatically segmenting the image into a plurality of regions by a first trained model; (c) automatically determining a boundary of a wound area of the wound or portion thereof by a second trained model based on the plurality of regions from segmentation; (d) determining three-dimensional characteristics of the wound area comprising a length, a width, and a depth of the wound or portion thereof, (e) determining a wound healing rate of the wound based on the three-dimensional characteristics of the wound area and using the equation:

$$V/P=-D(c)*t+q,$$

where V is a volume of wound, P is a perimeter of wound, Dc is a continuous linear healing rate, t is time in between evaluation, and q is time of closure.

In some embodiments, the method comprises determining the wound healing rate over a predetermined time period. In some embodiments, the method comprises determining the wound healing rate after the predetermined time period has lapsed.

In some embodiments, the method comprises predicting an area reduction of the wound or a portion thereof over the predetermined time period. In some embodiments, the step of predicting an area reduction of the wound or a portion thereof over the predetermined time period is performed by a third trained model.

In some embodiments, the method comprises determining an actual amount of area reduction of the wound or portion thereof over the predetermined time period. In some embodiments, the method comprises updating the third trained model with new training data comprising at least the image of the wound or portion thereof and the actual amount of area reduction of the wound or portion thereof.

In some embodiments, the method comprises determining an expected time period needed for the wound or portion thereof to heal. In some embodiments, the method comprises determining the wound healing rate after the expected time period needed for the wound or portion thereof to heal.

In some embodiments, the method comprises selecting, prior to an end of the predetermined time period, between a standard wound care therapy and an advanced wound care therapy based at least in part on the wound healing rate.

In some embodiments, the method comprises comparing a historical wound healing rate and the wound healing rate.

In some embodiments, the first trained model, the second trained model, or the third trained model comprises one or more machine learning models. In some embodiments, the one or more machine learning models comprise a classifier. In some embodiments, the one or more machine learning models comprise a neural network, a convolutional neural network (CNN), a deep convolutional neural network (DCNN), a cascaded deep convolutional neural network, a simplified CNN, a shallow CNN, or a combination thereof.

In some embodiments, the one or more machine learning models are trained using a wound, burn, or ulcer image set.

In some embodiments, the three-dimensional characteristics of the wound area comprise topology information of the wound area.

In some embodiments, the wound is caused by injury, skin lesion, and/or tissue abnormality. In some embodiments, the method comprises identifying the wound or portion thereof as granulation, slough, or eschar tissue.

In some embodiments, the image data is acquired from an imaging device comprising one or more imaging sensors. In some embodiments, the imaging device is contained in a mobile device.

In another aspect, this disclosure also provides a system for determining a wound healing rate of a wound or a portion thereof on a subject, comprising one or more processors configured to implement the method as described herein.

The foregoing summary is not intended to define every aspect of the disclosure, and additional aspects are described in other sections, such as the following detailed description. The entire document is intended to be related as a unified disclosure, and it should be understood that all combinations of features described herein are contemplated, even if the combinations of features are not found together in the same sentence, or paragraph, or section of this document. Other features and advantages of the invention will become apparent from the following detailed description. It should be understood, however, that the detailed description and the specific examples, while indicating specific embodiments of the disclosure, are given by way of illustration only, because various changes and modifications within the spirit and scope of the disclosure will become apparent to those skilled in the art from this detailed description.

BRIEF DESCRIPTION OF THE DRAWINGS

FIG. 1 shows an example process to track wound healing according to various embodiments of this disclosure.

FIG. 3 shows an example process to facilitate wound healing according to various embodiments of this disclosure.

DETAILED DESCRIPTION

Figure 2:
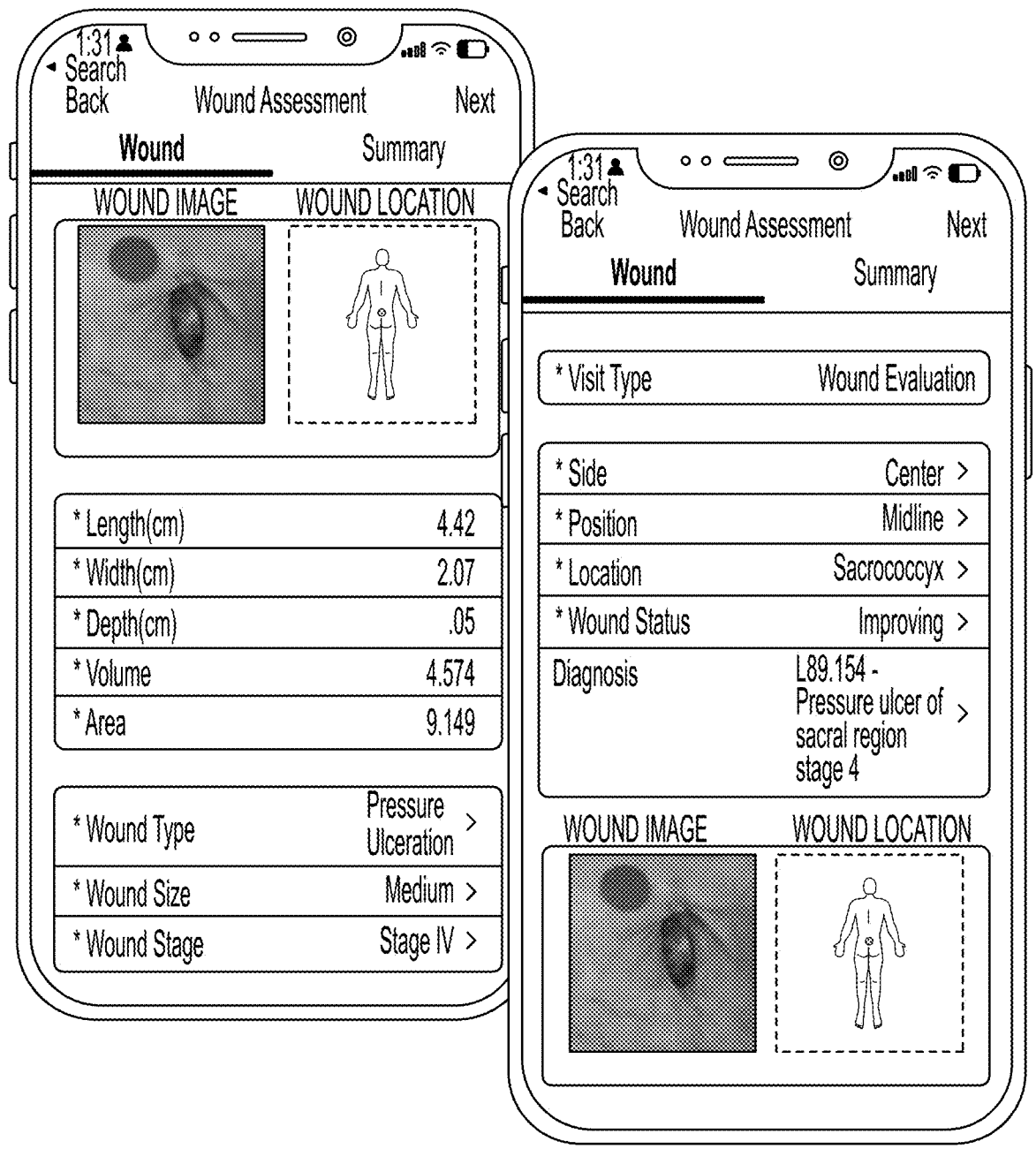
FIG. 2 shows an example process implemented on a mobile device. The process involves calculating three-dimensional information of a wound area, according to various embodiments of this disclosure.
Figure 4:
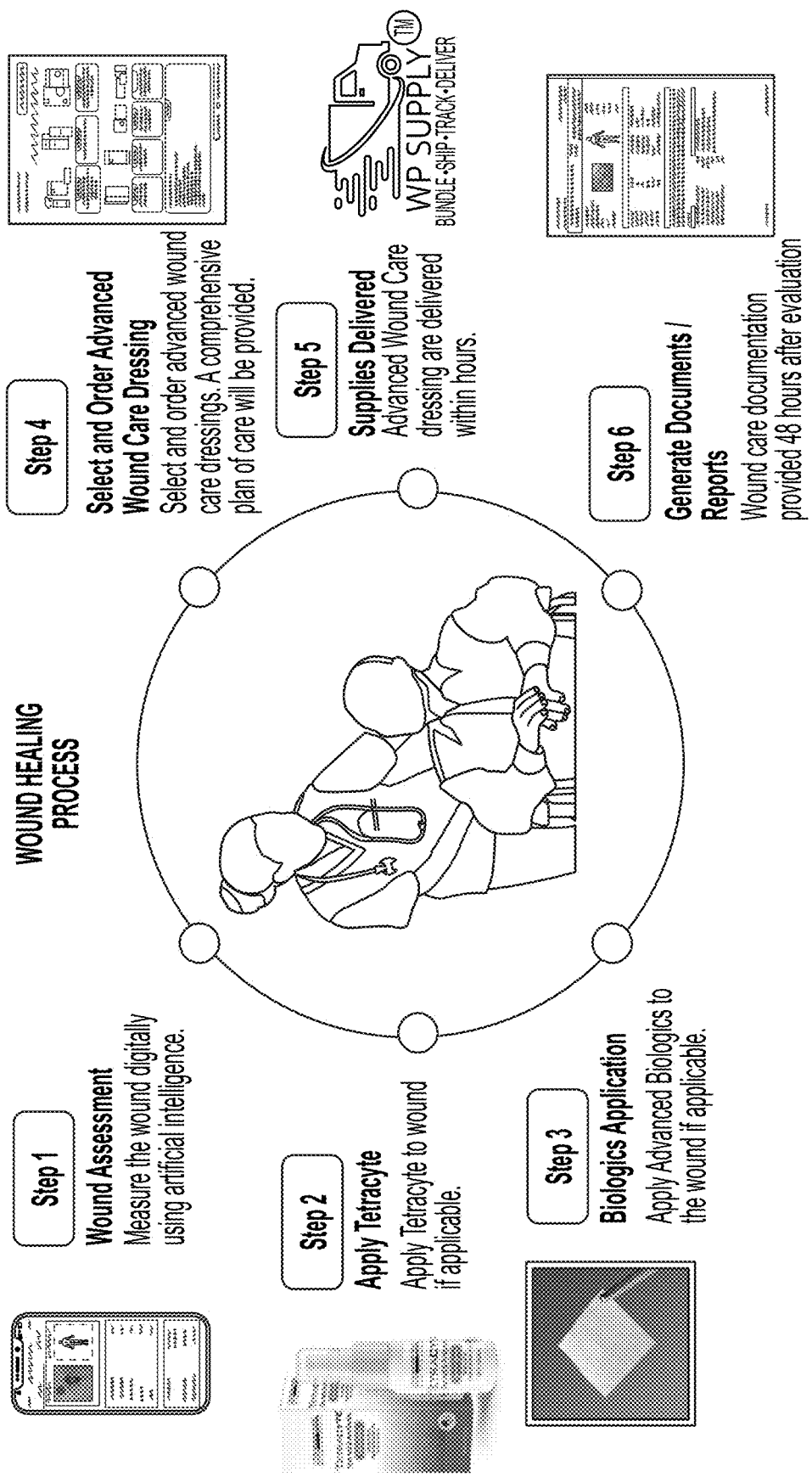
FIG. 4 shows an example wound healing process according to various embodiments of this disclosure.

This disclosure provides a novel method and system for wound assessment and treatment to improve wound healing. Objective assessment of wound healing progress is the basis for determining effectiveness of treatment, and is critical in selecting a suitable treatment plan. Few mathematical models in the literature deal with the complications associated with wound healing. Existing methods for assessment of wound status in terms of time are often based on measurements of wound area or wound perimeter. However, use of the existing methods is limited due at least to their low precision and poor performance in predicting wound healing rates. In contrast, the disclosed method and system determines wound healing rates and appropriate treatment plans by calculating volume of a wound based on three-dimensional wound information in wound images extracted by machine learning models.

While measurements of area of a wound are easier to carry out with simple tools like tracing paper or digital photographs and more suitable for superficial wounds with minimal depth, like abrasions, it is less precise for deeper wounds as they do not account for three-dimensional aspects of wounds. In contrast, wound volume measurement, as in the disclosed methods, is more reflective of the true extent of tissue damage and healing because it accounts for depth of wounds. It is particularly accurate for wounds that have significant depth, like pressure ulcers—a major challenge as our senior population is growing. For at least these reasons, the disclosed methods based on volume measurement can afford higher precision in assessing wound healing rates.

Moreover, the disclosed methods based on volume measurement provide a comprehensive view of healing, potentially leading to better tailored treatments, and can reveal subtleties in healing progress that area measurement might miss. However, volume measurement can require more sophisticated technology and expertise and can be time-consuming and costly. The disclosed methods address these challenges by providing a novel approach to assess wound healing rates by volume measurement based on three-dimensional wound information in wound images automatically extracted by machine learning models.

Accordingly, this disclosure provides novel methods and systems for determining a wound healing rate of a wound or a portion thereof on a subject. In some embodiments, the method may include: (a) obtaining image data comprising an image of a wound or a portion thereof of a subject; (b) automatically segmenting the image into a plurality of regions by a first trained model; (c) automatically determining a boundary of a wound area of the wound or portion thereof by a second trained model based on the plurality of regions from segmentation; (d) determining characteristics (e.g., three-dimensional characteristics) of the wound area, such as a length, a width, and a depth, of the wound or portion thereof, (e) determining a wound healing rate of the wound based on the three-dimensional characteristics of the wound area and using the equation:

$$V/P = -D(c)*t + q,$$

where V is a volume of wound, P is a perimeter of wound, Dc is a continuous linear healing rate, t is time in between evaluation, and q is time of closure.

In some embodiments, the method may include determining the characteristics of a wound area comprising cross-sectional and/or intra-volume variation in the size, area, depth, volume, shape, outline, texture, color, temperature, spectral absorption distribution, movement of the wound, injury, skin lesion, and/or tissue abnormality at a given point in time. In some embodiments, the method may include determining changes over time in the size, area, depth, volume, shape, outline, texture, color, temperature, spectral absorption distribution, movement of the wound, injury, skin lesion, and/or tissue abnormality.

A "wound" generally refers to tissue injury on a subject, which may include an opening in the subject's skin or may include unbroken skin that exhibits other injury characteristics, such as a contusion, redness, or the like. A wound is generally susceptible to inflammation, infection, and/or the like. One example of a wound is an ulcer, such as a pressure ulcer. Pressure ulcers may occur, for example, as the result of a bedridden subject being stationary in bed for an extended period of time. Pressure ulcers may be divided into four classes based on their severity, including Stage I ulcers where the skin remains intact with non-blanching redness, Stage II ulcers where the ulcer is shallow and open and has a pinkish wound bed, Stage III ulcers where a full thickness tissue loss has occurred such that subcutaneous fat is visible, and Stage IV ulcers where a full thickness tissue loss has occurred such that muscle and/or bone is visible. While the device described herein may generally be aimed at a target area that includes a wound, it should be understood that other objects, such as surgical scars, lesions (e.g., moles), anatomical features surrounding the wound, and/or the like may also be imaged without departing from the scope of the present disclosure.

In some embodiments, the wound is caused by injury, skin lesion, and/or tissue abnormality. In some embodiments, the method may include identifying the wound or portion thereof as granulation, slough, or eschar tissue.

In some embodiments, the three-dimensional characteristics of the wound area may include topology information of the wound area.

The terms "patient," "subject," "host," and "individual" are used interchangeably herein and refer to any subject, particularly a vertebrate subject, and even more particularly a mammalian subject, for whom therapy or prophylaxis is desired. Suitable vertebrate animals that fall within the scope of the invention include, but are not restricted to, any member of the subphylum Chordata including primates (e.g., humans, monkeys and apes, and includes species of monkeys such from the genus *Macaca* (e.g., cynomolgus monkeys such as *Macaca fascicularis*, and/or rhesus monkeys (*Macaca mulatta*)) and baboon (*Papio ursinus*), as well as marmosets (species from the genus *Callithrix*), squirrel monkeys (species from the genus *Saimiri*) and tamarins (species from the genus *Saguinus*), as well as species of apes such as chimpanzees (Pan troglodytes)), rodents (e.g., mice rats, guinea pigs), lagomorphs (e.g., rabbits, hares), bovines (e.g., cattle), ovines (e.g., sheep), caprines (e.g., goats), porcines (e.g., pigs), equines (e.g., horses), canines (e.g., dogs), felines (e.g., cats), avians (e.g., chickens, turkeys, ducks, geese, companion birds such as canaries, budgerigars etc.), marine mammals (e.g., dolphins, whales), reptiles (snakes, frogs, lizards etc.), and fish. In some embodiments, a subject is a human with a peripheral nervous system disorder.

As used herein, the term "images" or "image" refers video images (i.e., a sequence of consecutive images) and/or still images (including still images isolated from video images) that are captured by the imaging device. Any suitable commercially available imaging device may be used without departing from the scope of the present disclosure. In some embodiments, the imaging device may be coupled to one or more other components that provide additional functionality for imaging, such as a thermal imaging device. In some embodiments, the image data may include two-dimensional or three-dimensional imaging data. In some embodiments, the image data may include time-lapse imaging data, a video, or live video streaming data. As used herein, the term "image" or "images" refers to single or multiple frames of still or animated images, video clips, video streams, etc. Preprocessing may include detecting an image in the image of the subject by the user device. Preprocessing may also include cropping, resizing, gradation conversion, median filtering, histogram equalization, or size-normalized image processing. In some embodiments, the method may include resizing the photo or the videos according to a threshold value (e.g., maximum size in kilobytes, megabytes or gigabytes, maximum or minimum resolution in dots per inch (DPI) or pixels per inch (PPI)).

Chronic wounds often require constant monitoring and attention. Beyond the visual information that can be obtained by a traditional single 2D camera, the three dimensional surface data is of particular clinical relevance.

In some embodiments, the method may include determining the wound healing rate over a predetermined time period. In some embodiments, the method may include determining the wound healing rate after the predetermined time period has lapsed.

In some embodiments, the method may include predicting an area reduction of the wound or a portion thereof over the predetermined time period. In some embodiments, the step of predicting an area reduction of the wound or a portion thereof over the predetermined time period is performed by a third trained model.

In some embodiments, segmenting the image may include segmentation of the image into a wound portion and a non-wound portion of the image.

In some embodiments, the method may include determining an actual amount of area reduction of the wound or portion thereof over the predetermined time period. In some embodiments, the method may include updating the third trained model with new training data comprising at least the image of the wound or portion thereof and the actual amount of area reduction of the wound or portion thereof.

In some embodiments, the method may include determining an expected time period needed for the wound or portion thereof to heal. In some embodiments, the method may include determining the wound healing rate after the expected time period needed for the wound or portion thereof to heal.

In some embodiments, the method may include determining an appropriate level of wound care therapy based on the results of the machine learning models disclosed herein. In some embodiments, the method may include selecting, prior to an end of the predetermined time period, between a standard wound care therapy and an advanced wound care therapy based at least in part on the wound healing rate. For example, if the method indicates that an imaged wound will close by more than 50% within 30 days, it can apply or inform a health care practitioner or patient to apply a standard of care therapy; if the method indicates that the wound will not close by more than 50% in 30 days, it can apply or inform the health care practitioner or patient to use one or more advanced wound care therapies.

Under existing wound treatment, a wound such as a diabetic foot ulcer (DFU) may initially receive one or more standard wound care therapies for the initial 30 days of treatment, such as standard of care (SOC) therapy as defined by the Centers for Medicare and Medicaid. As one example of a standard wound care regimen, a standard of care therapy can include one or more of: optimization of nutritional status; debridement by any means to remove devitalized tissue; maintenance of a clean, moist bed of granulation tissue with appropriate moist dressings; necessary treatment to resolve any infection that may be present; addressing any deficiencies in vascular perfusion to the extremity with the diabetic foot ulcer; offloading of pressure from the diabetic foot ulcer; and appropriate glucose control. During this initial period of 30 days of the standard of care therapy, measurable signs of diabetic foot ulcer healing are defined as: decrease in size of diabetic foot ulcer (either wound surface area or wound volume), decrease in amount of diabetic foot ulcer exudate, and decrease in amount of necrotic tissue within the diabetic foot ulcer.

If healing is not observed during this initial period of 30 days of the standard of care therapy, advanced wound care (AWC) therapies are generally indicated. The Centers for Medicare and Medicaid have no summary or definition of advanced wound care therapies but are considered to be any therapy outside of the standard of care therapy as defined above. Advanced wound care therapies are an area of intense research and innovation with near-constant introduction of new options to be used in clinical practice. Therefore, coverage of advanced wound care therapies is determined on an individual basis and a treatment considered advanced wound care may not be covered for reimbursement for some patients. Based on this understanding, advanced wound care therapies include, but are not limited to, any one or more of: hyperbaric oxygen therapy; negative-pressure wound therapy; bioengineered skin substitutes; synthetic growth factors; extracellular matrix proteins; matrix metalloproteinase modulators; and electrical stimulation therapy.

In some embodiments, the method may include comparing a historical wound healing rate and the wound healing rate. In some embodiments, a historical wound healing rate may be determined at any prior time point or over a prior time period.

In some embodiments, the first trained model, the second trained model, or the third trained model may include one or more machine learning models. In some embodiments, the first trained model and the second trained model are the same model.

In some embodiments, the one or more machine learning models may include a classifier.

Artificial neural networks are artificial in the sense that they are computational entities, inspired by biological neural networks but modified for implementation by computing devices. Artificial neural networks are used to model complex relationships between inputs and outputs or to find patterns in data, where the dependency between the inputs and the outputs cannot be easily ascertained. A neural network typically includes an input layer, one or more intermediate ("hidden") layers, and an output layer, with each layer including a number of nodes. The number of nodes can vary between layers. A neural network is considered "deep" when it includes two or more hidden layers. The nodes in each layer connect to some or all nodes in the subsequent layer and the weights of these connections are typically learned based on training data during the training process, for example, through backpropagation in which the network parameters are tuned to produce expected outputs given corresponding inputs in labeled training data. Thus, an artificial neural network may be an adaptive system that is configured to change its structure (e.g., the connection configuration and/or weights) based on information that flows through the network during training, and the weights of the hidden layers can be considered as an encoding of meaningful patterns in the data.

A fully connected neural network is one in which each node in the input layer is connected to each node in the subsequent layer (the first hidden layer), each node in that first hidden layer is connected in turn to each node in the subsequent hidden layer, and so on until each node in the final hidden layer is connected to each node in the output layer.

Autoencoders are neural networks that include an encoder and a decoder. The goal of certain autoencoders is to compress the input data with the encoder, then decompress this encoded data with the decoder such that the output is a good/perfect reconstruction of the original input data. Example autoencoder neural networks described herein can take the image pixel values of an image of a wound (e.g., structured in vector or matrix form) as inputs into its input layer. The subsequent one or more layers, or "encoder layers," encode this information by lowering its dimensionality (e.g., by representing the input using fewer dimensions than its original n-dimensions), and the additional one or more hidden layers subsequent to the encoder layers ("decoder layers") decode this information to generate an output feature vector at the output layer. An example training process for the autoencoder neural network can be unsupervised, in that the autoencoder learns the parameters of its hidden layers that produce the same output as the provided input. As such, the number of nodes in the input and output layers are typically the same. The dimensionality reduction allows the autoencoder neural network to learn the most salient features of the input images, where the innermost layer (or another inner layer) of the autoencoder represents a "feature reduction" version of the input. In some examples, this can serve to reduce an image having, for example, approximately 1 million pixels (where each pixel value can be considered as a separate feature of the image) to a feature set of around 50 values. This reduced-dimensionality representation of the images can be used by another machine learning model or a suitable CNN or other neural network, in order to output a predicted healing parameter.

A CNN is a type of artificial neural network, and like the artificial neural networks described above, a CNN is made up of nodes and has learnable weights between nodes. However, the layers of a CNN can have nodes arranged in three dimensions: width, height, and depth, corresponding to the 2×2 array of pixel values in each image frame (e.g., the width and height) and to the number of image frames in a sequence of images (e.g., the depth). In some embodiments, the nodes of a layer may only be locally connected to a small region of the width and height of the preceding layer, called a receptive field. The hidden layer weights can take the form of a convolutional filter applied to the receptive field. In some embodiments, the convolutional filters can be two-dimensional, and thus, convolutions with the same filter can be repeated for each frame (or convolved transformation of an image) in the input volume or for designated subset of the frames. In other embodiments, the convolutional filters can be three-dimensional and thus extend through the full depth of nodes of the input volume. The nodes in each convolutional layer of a CNN can share weights such that the convolutional filter of a given layer is replicated across the entire width and height of the input volume (e.g., across an entire frame), reducing the overall number of trainable weights and increasing applicability of the CNN to data sets outside of the training data. Values of a layer may be pooled to reduce the number of computations in a subsequent layer (e.g., values representing certain pixels may be passed forward while others are discarded), and further along the depth of the CNN pool masks may reintroduce any discarded values to return the number of data points to the previous size. A number of layers, optionally with some being fully connected, can be stacked to form the CNN architecture. During training, an artificial neural network can be exposed to pairs in its training data and can modify its parameters to be able to predict the output of a pair when provided with the input.

Artificial intelligence describes computerized systems that can perform tasks typically considered to require human intelligence. Here, the disclosed artificial intelligence systems can perform image (and other data) analysis that, without the disclosed technology, may otherwise require the skill and intelligence of a human physician. Beneficially, the disclosed artificial intelligence systems can make such predictions upon an initial patient visit rather than requiring a wait time of 30 days to assess wound healing.

As used herein, a "machine learning model," a "model," or a "classifier" refers to a set of algorithmic routines and parameters that can predict an output(s) for a process input based on a set of input features, with or without being explicitly programmed. A structure of the software routines (e.g., number of subroutines and relation between them) and/or the values of the parameters can be determined in a training process, which can use actual results of the process that is being modeled. Such systems or models are understood to be necessarily rooted in computer technology, and in fact, cannot be implemented or even exist in the absence of computing technology. While machine learning systems utilize various types of statistical analyses, machine learning systems are distinguished from statistical analyses by virtue of the ability to learn without explicit programming and being rooted in computer technology. A neural network or an artificial neural network is one set of algorithms used in machine learning for modeling the data using graphs of neurons. Any network structure may be used. Any number of layers, nodes within layers, types of nodes (activations), types of layers, interconnections, learnable parameters, and/or other network architectures may be used. Machine training uses the defined architecture, training data, and optimization to learn values of the learnable parameters of the architecture based on the samples and ground truth of training data.

A typical machine learning pipeline may include building a machine learning model from a sample dataset (referred to as a "training set"), evaluating the model against one or more additional sample datasets (referred to as a "validation set" and/or a "test set") to decide whether to keep the model and to benchmark how good the model is, and using the model in "production" to make predictions or decisions against live input data captured by an application service. For training the model to be applied as a machine-learned model, training data is acquired and stored in a database or memory. The training data is acquired by aggregation, mining, loading from a publicly or privately formed collection, transfer, and/or access. Ten, hundreds, or thousands of samples of training data are acquired. The samples are from scans of different patients and/or phantoms. Simulation may be used to form the training data. The training data includes the desired output (ground truth), such as segmentation, and the input, such as protocol data and imaging data.

In some embodiments, the training set will be used to create a single classifier using any now or hereafter-known methods. In other embodiments, a plurality of training sets will be created to generate a plurality of corresponding classifiers. Each of the plurality of classifiers can be generated based on the same or different learning algorithm that utilizes the same or different features in the corresponding one of the pluralities of training sets.

Once trained, the machine-learned or trained classifier is stored for later application. The training determines the values of the learnable parameters of the network. The network architecture, values of non-learnable parameters, and values of the learnable parameters are stored as the machine-learned network. Once stored, the machine-learned network may be fixed. The same machine-learned network may be applied to different patients, different scanners, and/or with different imaging protocols for the scanning. The machine-learned network may be updated. As additional training data is acquired, such as through application of the network for patients and corrections by experts to that output, the additional training data may be used to re-train or update the training.

For the machine learning model, input data structures of subreads can be used for the training. The input data structure may correspond to a window of in a sequence. The training is performed by optimizing parameters of the model based on outputs of the model matching or not matching corresponding labels of the first labels and optionally the second labels when the first plurality of first data structures and optionally the second plurality of second data structures are input to the model. In some embodiments, the output of the model may include a probability of being in each of a plurality of states. The state with the highest probability can be taken as the state.

In some embodiments, the machine learning model may further include a supervised learning model. Supervised learning models may include different approaches and algorithms including analytical learning, artificial neural network, backpropagation, boosting (meta-algorithm), Bayesian statistics, case-based reasoning, decision tree learning, inductive logic programming, Gaussian process regression, genetic programming, group method of data handling, kernel estimators, learning automata, learning classifier systems, minimum message length (decision trees, decision graphs, etc.), multilinear subspace learning, naive Bayes classifier, maximum entropy classifier, conditional random field, Nearest Neighbor Algorithm, probably approximately correct learning (PAC) learning, ripple down rules, a knowledge acquisition methodology, symbolic machine learning algorithms, subsymbolic machine learning algorithms, support vector machines, Minimum Complexity Machines (MCM), random forests, ensembles of classifiers, ordinal classification, data pre-processing, handling imbalanced datasets, statistical relational learning, or Proaftn, a multi-criteria classification algorithm, linear regression, logistic regression, deep recurrent neural network (e.g., long short term memory, LSTM), Bayes classifier, hidden Markov model (HMM), linear discriminant analysis (LDA), k-means clustering, density-based spatial clustering of applications with noise (DBSCAN), random forest algorithm, support vector machine (SVM), or any model described herein.

As used herein, the term "classifiers" refers generally to various types of classifier frameworks, such as neural network classifiers, hierarchical classifiers, ensemble classifiers, etc. In addition, a classifier design can include a multiplicity of classifiers that attempt to partition data into two groups, either organized hierarchically or run in parallel, and then combined to find the best classification. Further, a classifier can include ensemble classifiers wherein a large number of classifiers all attempting to perform the same classification task are learned, but trained with different data/variables/parameters, and then combined to produce a final classification label. The classification methods implemented may be "black boxes" that are unable to explain their prediction to a user (which is the case if classifiers are built using neural networks, for example). The classification methods may be "white boxes" that are in a human-readable form (which is the case if classifiers are built using decision trees, for example). In other embodiments, the classification models may be "gray boxes" that can partially explain how solutions are derived (e.g., a combination of "white box" and "black box" type classifiers).

As used herein, the term "classification" refers to any number or other characters that are associated with a particular property of a sample. The classification can be binary (e.g., positive or negative) or have more levels of classification (e.g., a scale from 1 to 10 or 0 to 1). The term "cutoff" or "threshold" refers to a predetermined number used in an operation. For example, a cutoff value can refer to a classification score as used above. A threshold value may be a value above or below which a particular classification applies. Either of these terms can be used in either of these contexts.

In some embodiments, the classifier may include a supervised or unsupervised Machine Learning or Deep Learning algorithm, Logistic Regression, Naive Bayes, Support Vector Machine, Decision Tree, Random Forest, Gradient Boosting, Regularizing Gradient Boosting, K-Nearest Neighbors, a continuous regression approach, Ridge Regression, Kernel Ridge Regression, Support Vector Regression, deep learning approach, Neural Networks, Convolutional Neural Network (CNNs), Recurrent Neural Networks (RNNs), Gated Recurrent Units (GRUs), Long Short Term Memory Networks (LSTMs), Generative Models, Generative Adversarial Networks (GANs), Deep Belief Networks (DBNs), Feedforward Neural Networks, Autoencoders, Variational Autoencoders, Normalizing Flow Models, Denoising Diffusion Probabilistic Models (DDPMs), Score Based Generative Models (SGMs), Radial Basis Function Networks (RBFNs), Multilayer Perceptrons (MLPs), Stochastic Neural Networks, or any combination thereof.

In some embodiments, the model may include a convolutional neural network (CNN). The CNN may include a set of convolutional filters configured to filter the first plurality of data structures and, optionally, the second plurality of data structures. The filter may be any filter described herein. The number of filters for each layer may be from 10 to 20, 20 to 30, 30 to 40, 40 to 50, 50 to 60, 60 to 70, 70 to 80, 80 to 90, 90 to 100, 100 to 150, 150 to 200, or more. The kernel size for the filters can be 2, 3, 4, 5, 6, 7, 8, 9, 10, 11, 12, 13, 14, 15, from 15 to 20, from 20 to 30, from 30 to 40, or more. The CNN may include an input layer configured to receive the filtered first plurality of data structures and, optionally, the filtered second plurality of data structures. The CNN may also include a plurality of hidden layers, including a plurality of nodes. The first layer of the plurality of hidden layers is coupled to the input layer. The CNN may further include an output layer coupled to a last layer of the plurality of hidden layers and configured to output an output data structure. The output data structure may include the properties.

As used herein, the terms or acronyms like "convolutional neural network," "CNN," "neural network," "NN," "deep neural network," "DNN," "recurrent neural network," "RNN," and/or the like may be interchangeably referenced throughout this document.

In some embodiments, the one or more machine learning models may include a neural network, a convolutional neural network (CNN), a deep convolutional neural network (DCNN), a cascaded deep convolutional neural network, a simplified CNN, a shallow CNN, or a combination thereof.

In some embodiments, the one or more machine learning models are trained using a wound, burn, or ulcer image set.

In another aspect, this disclosure also provides a system for determining a wound healing rate of a wound or a portion thereof on a subject, comprising one or more processors configured to implement the method as described herein.

In some embodiments, the image data is acquired from an imaging device comprising one or more imaging sensors, e.g., a sensor array. The image sensor array may generally be any commercially available image sensor array, such as, for example, a charge-coupled device (CCD) or an active pixel sensor in a complementary metal-oxide semiconductor (CMOS) or N-type metal-oxide semiconductor (NMOS) array. As such, it should be understood that the image sensor array may be constructed of a plurality of rows and columns of pixels. For example, the image sensor array may be arranged as a grid having about 1500 pixels by about 1152 pixels, about 1280 pixels by about 1024 pixels, or about 640 pixels by about 480 pixels. In some embodiments, a size of each pixel in the image sensor array may be such that the length and width of each pixel is about 6 micrometers (μm) by about 6 μm, about 4 μm by about 4 μm, about 2 μm by about 2 μm, about 1 μm by about μm, or the like.

In some embodiments, the imaging device is contained in a handheld device, e.g., a mobile device (e.g., a smartphone, a tablet, a wearable device).

As used herein, a "handheld device" generally refers to a device that is generally portable in nature such that it can be held and manipulated by a single user. As such, a handheld device may have dimensional characteristics (e.g., shape, size, etc.) that allow for holding and manipulation by a single user. Accordingly, the device may be configured and designed such that a single user such as the subject, a friend of the subject, a family member of the subject, a caretaker of the subject, other non-medical personnel, and/or the like can hold and manipulate the device in a manner as described herein.

In some embodiments, the device may include a plurality of modular components such that various components may be removably coupled or attached to the device. For example, in some embodiments, the device may include a computing device that may be removably attached to the device or may be used as a separate component, e.g., a mobile device such as a mobile phone or the like that contains software for carrying out the various processes described herein.

In some embodiments, the device may include a display arranged in such a way that images that are received from an imaging component and information and/or images are displayed to one or more individuals operating the device when the device is positioned to image a target object.

In some embodiments, the device may include an imaging device, one or more light emitting components, and/or one or more laser emitting devices. The one or more light emitting components and the one or more laser emitting devices may generally be arranged and positioned such that the imaging device, the one or more light emitting components, and the one or more laser emitting devices are all aimed in the same general direction. In some embodiments, the imaging device may be positioned to image a target area that is illuminated by the one or more light emitting components and/or receives a projection from the one or more laser emitting devices. For example, an optical axis A of the imaging device extends towards at least a portion of a subject and/or one or more wounds thereon when aimed by a user. In the embodiments described herein, the optical axis A refers to an imaginary line defining the path along which electromagnetic radiation (such as light) propagates to and through the imaging device.

In some embodiments, components of the device are communicatively coupled to each other to transmit data. For example, the computing device is communicatively coupled to the imaging component such that the computing device receives data transmissions, particularly data transmissions containing image data, from the imaging component. In some embodiments, the imaging component and the computing device may be connected via a network. The network may include a wide area network (WAN), such as the Internet, a local area network (LAN), a mobile communications network, a public service telephone network (PSTN), a personal area network (PAN), a metropolitan area network (MAN), a virtual private network (VPN), a mesh network, or any other suitable network. In other embodiments, the imaging device and the computing device may be directly connected to one another. In addition, the imaging device and the computing device may be communicatively connected to one another via any means of wireless or wired communication, such as, but not limited to one or more wires, cables, and/or the like, one or more wireless radios such as, for example, a Bluetooth radio, an 802.11 standard radio, a near field communication (NFC) radio, a radio frequency (RF) radio, and/or the like.

In another aspect, this disclosure provides a system for complementarity-adjusted federated averaging imputation. In some embodiments, the system may include one or more processors configured to implement the method as described herein.

Figure 5:
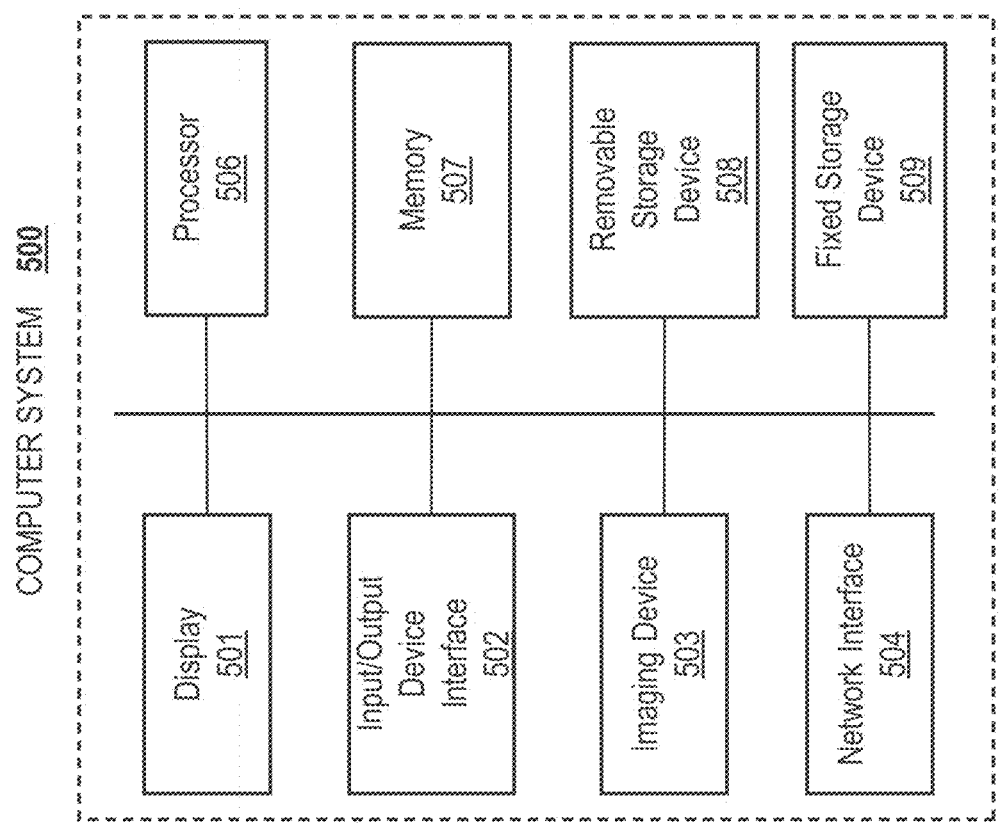
FIG. 5 shows an example computing architecture for implementing the disclosed methods.

FIG. 5 is a functional diagram illustrating a programmed computer system in accordance with some embodiments. As will be apparent, other computer system architectures and configurations can be used to perform the described methods. Computer system 500, which includes various subsystems as described below, includes at least one microprocessor subsystem (also referred to as a processor or a central processing unit (CPU) 506). For example, processor 506 can be implemented by a single-chip processor or by multiple processors. In some embodiments, processor 506 is a general-purpose digital processor that controls the operation of the computer system 500. In some embodiments, processor 506 also includes one or more coprocessors or special purpose processors (e.g., a graphics processor, a network processor, etc.). Using instructions retrieved from memory 507, processor 506 controls the reception and manipulation of input data received on an input device (e.g., image processing device 503, I/O device interface 502), and the output and display of data on output devices (e.g., display 501).

Processor 506 is coupled bi-directionally with memory 507, which can include, for example, one or more random access memories (RAM) and/or one or more read-only memories (ROM). As is well known in the art, memory 507 can be used as a general storage area, a temporary (e.g., scratchpad) memory, and/or a cache memory. Memory 507 can also be used to store input data and processed data, as well as to store programming instructions and data, in the form of data objects and text objects, in addition to other data and instructions for processes operating on processor 506. Also, as is well known in the art, memory 507 typically includes basic operating instructions, program code, data, and objects used by the processor 506 to perform its functions (e.g., programmed instructions). For example, memory 507 can include any suitable computer-readable storage media described below, depending on whether, for example, data access needs to be bi-directional or unidirectional. For example, processor 506 can also directly and very rapidly retrieve and store frequently needed data in a cache memory included in memory 507.

A removable mass storage device 508 provides additional data storage capacity for the computer system 500 and is optionally coupled either bi-directionally (read/write) or unidirectionally (read-only) to processor 506. A fixed mass storage 509 can also, for example, provide additional data storage capacity. For example, storage devices 508 and/or 509 can include computer-readable media such as magnetic tape, flash memory, PC-CARDS, portable mass storage devices such as hard drives (e.g., magnetic, optical, or solid-state drives), holographic storage devices, and other storage devices. Mass storages 508 and/or 509 generally store additional programming instructions, data, and the like that typically are not in active use by the processor 506. It will be appreciated that the information retained within mass storages 508 and 509 can be incorporated, if needed, in a standard fashion as part of memory 507 (e.g., RAM) as virtual memory.

In addition to providing processor 506 access to storage subsystems, bus 510 can be used to provide access to other subsystems and devices as well. As shown, these can include a display 501, a network interface 504, an input/output (I/O) device interface 502, an image processing device 503, as well as other subsystems and devices. For example, image processing device 503 can include a camera, a scanner, etc.; I/O device interface 502 can include a device interface for interacting with a touchscreen (e.g., a capacitive touch sensitive screen that supports gesture interpretation), a microphone, a sound card, a speaker, a keyboard, a pointing device (e.g., a mouse, a stylus, a human finger), a global positioning system (GPS) receiver, a differential global positioning system (DGPS) receiver, an accelerometer, and/or any other appropriate device interface for interacting with system 500. Multiple I/O device interfaces can be used in conjunction with computer system 500. The I/O device interface can include general and customized interfaces that allow the processor 506 to send and, more typically, receive data from other devices such as keyboards, pointing devices, microphones, touchscreens, transducer card readers, tape readers, voice or handwriting recognizers, biometrics readers, cameras, portable mass storage devices, and other computers.

The network interface 504 allows processor 506 to be coupled to another computer, computer network, or telecommunications network using a network connection as shown. For example, through the network interface 504, the processor 506 can receive information (e.g., data objects or program instructions) from another network, or output information to another network in the course of performing method/process steps. Information, often represented as a sequence of instructions to be executed on a processor, can be received from and outputted to another network. An interface card or similar device and appropriate software implemented by (e.g., executed/performed on) processor 506 can be used to connect the computer system 500 to an external network and transfer data according to standard protocols. For example, various process embodiments disclosed herein can be executed on processor 506 or can be performed across a network such as the Internet, intranet networks, or local area networks, in conjunction with a remote processor that shares a portion of the processing. Additional mass storage devices (not shown) can also be connected to processor 506 through network interface 504.

In addition, various embodiments disclosed herein further relate to computer storage products with a computer-readable medium that includes program code for performing various computer-implemented operations. The computer-readable medium includes any data storage device that can store data that can thereafter be read by a computer system. Examples of computer-readable media include, but are not limited to: magnetic media such as disks and magnetic tape; optical media such as CD-ROM disks; magneto-optical media such as optical disks; and specially configured hardware devices such as application-specific integrated circuits (ASICs), programmable logic devices (PLDs), and ROM and RAM devices. Examples of program code include both machine code as produced, for example, by a compiler, or files containing higher level code (e.g., script) that can be executed using an interpreter.

The computer system as shown in FIG. 5 is an example of a computer system suitable for use with the various embodiments disclosed herein. Other computer systems suitable for such use can include additional or fewer subsystems. In some computer systems, subsystems can share components (e.g., for touchscreen-based devices such as smartphones, tablets, etc., I/O device interface 502 and display 501 share the touch-sensitive screen component, which both detects user inputs and displays outputs to the user). In addition, bus 510 is illustrative of any interconnection scheme serving to link the subsystems. Other computer architectures having different configurations of subsystems can also be utilized.

Additional Definitions

To aid in understanding the detailed description of the compositions and methods according to the disclosure, a few express definitions are provided to facilitate an unambiguous disclosure of the various aspects of the disclosure. Unless otherwise defined, all technical and scientific terms used herein have the same meaning as commonly understood by one of ordinary skill in the art to which this disclosure belongs.

An "electronic device" or a "computing device" refers to a device that includes a processor and memory. Each device may have its own processor and/or memory, or the processor and/or memory may be shared with other devices as in a virtual machine or container arrangement. The memory will contain or receive programming instructions that, when executed by the processor, cause the electronic device to perform one or more operations according to the programming instructions.

As used herein, the terms "memory," "memory device," "computer-readable storage medium," "data store," "data storage facility," and the like each refer to a non-transitory device on which computer-readable data, programming instructions or both are stored. Except where specifically stated otherwise, the terms "memory," "memory device," "computer-readable storage medium," "data store," "data storage facility," and the like are intended to include single device embodiments, embodiments in which multiple memory devices together or collectively store a set of data or instructions, as well as individual sectors within such devices.

As used herein, the terms "processor" and "processing device" refer to a hardware component of an electronic device that is configured to execute programming instructions. Except where specifically stated otherwise, the singular term "processor" or "processing device" is intended to include both single-processing device embodiments and embodiments in which multiple processing devices together or collectively perform a process.

In this document, the terms "communication link" and "communication path" mean a wired or wireless path via which a first device sends communication signals to and/or receives communication signals from one or more other devices. Devices are "communicatively connected" if the devices are able to send and/or receive data via a communication link. "Electronic communication" refers to the transmission of data via one or more signals between two or more electronic devices, whether through a wired or wireless network, and whether directly or indirectly via one or more intermediary devices.

The terms "instructions" and "programs" may be used interchangeably herein. The instructions may be stored in object code format for direct processing by the processor, or in any other computing device language, including scripts or collections of independent source code modules that are interpreted on demand or compiled in advance. Functions, methods, and routines of the instructions are explained in more detail below. The instructions may be any set of instructions to be executed directly (such as machine code) or indirectly (such as scripts) by the processor. For example, the instructions may be stored as computing device code on the computing device-readable medium.

In addition, the terms "unit," "-er," "-or," and "module" described in the specification mean units for processing at least one function and operation, and can be implemented by hardware components or software components and combinations thereof.

The computer-readable storage medium can be a tangible device that can retain and store instructions for use by an instruction execution device. The computer-readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer-readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer-readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer-readable program instructions described herein can be downloaded to respective computing/processing devices from a computer-readable storage medium or to an external computer or external storage device via a network, for example, the Internet, a local area network, a wide area network and/or a wireless network. The network may include copper transmission cables, optical transmission fibers, wireless transmission, routers, firewalls, switches, gateway computers and/or edge servers. A network adapter card or network interface in each computing/processing device receives computer-readable program instructions from the network and forwards the computer-readable program instructions for storage in a computer-readable storage medium within the respective computing/processing device.

Computer-readable program instructions for carrying out operations of the present invention may be assembler instructions, instruction-set-architecture (ISA) instructions, machine instructions, machine-dependent instructions, microcode, firmware instructions, state-setting data, or either source code or object code written in any combination of one or more programming languages, including an object-oriented programming language such as Smalltalk, C++ or the like, and conventional procedural programming languages, such as the "C" programming language or similar programming languages. The computer-readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

These computer-readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer-readable program instructions may also be stored in a computer-readable storage medium that can direct a computer, a programmable data processing apparatus, and/or other devices to function in a particular manner, such that the computer-readable storage medium having instructions stored therein comprises an article of manufacture including instructions which implement aspects of the function/act specified in the flowchart and/or block diagram block or blocks.

The computer-readable program instructions may also be loaded onto a computer, other programmable data processing apparatus, or other device to cause a series of operational steps to be performed on the computer, other programmable apparatus or other device to produce a computer-implemented process, such that the instructions which execute on the computer, other programmable apparatus, or other device implement the functions/acts specified in the flowchart and/or block diagram block or blocks.

Aspects of the present disclosure are described herein with reference to flowchart illustrations and/or block diagrams of methods, apparatus (systems), and computer program products according to embodiments of the invention. In some embodiments, the flowchart and block diagrams in the Figures illustrate the architecture, functionality, and operation of possible implementations of systems, methods, and computer program products according to various embodiments of the present invention. In this regard, each block in the flowchart or block diagrams may represent a module, a segment, or a portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Unless specifically stated otherwise, it is appreciated that throughout the disclosure, descriptions utilizing terms such as "obtaining," "performing," "receiving," "computing," "associating," "assigning," "traversing," "calculating," "determining," "identifying," "transforming," "ranking," "providing," "transmitting," or the like, refer to the action and processes of a computer system, or similar electronic computing device, that manipulates and transforms data represented as physical (or electronic) quantities within the computer system memories or registers or other such information storage, transmission or display devices.

As used herein, the term "logistic regression" is a regression model for binary data from statistics where the logit of the probability that the dependent variable is equal to one is modeled as a linear function of the dependent variables.

As used herein, the term "neural network" is a machine learning model for classification or regression consisting of multiple layers of linear transformations followed by element-wise nonlinearities typically trained via stochastic gradient descent and back-propagation.

The term "machine learning," as used herein, refers to a computer algorithm used to extract useful information from a database by building probabilistic models in an automated way.

The term "regression tree," as used herein, refers to a decision tree that predicts values of continuous variables.

As used herein, the term "if may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

It will be understood that, although the terms "first," "second," etc., may be used herein to describe various elements, components, regions, layers and/or sections. These elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of example embodiments.

It is noted here that, as used in this specification and the appended claims, the singular forms "a," "an," and "the" include plural reference unless the context clearly dictates otherwise. The terms "including," "comprising," "containing," or "having" and variations thereof are meant to encompass the items listed thereafter and equivalents thereof as well as additional subject matter unless otherwise noted.

The phrases "in one embodiment," "in various embodiments," "in some embodiments," and the like are used repeatedly. Such phrases do not necessarily refer to the same embodiment, but they may unless the context dictates otherwise.

The terms "and/or" or "/" means any one of the items, any combination of the items, or all of the items with which this term is associated.

As used herein, the term "each," when used in reference to a collection of items, is intended to identify an individual item in the collection but does not necessarily refer to every item in the collection. Exceptions can occur if explicit disclosure or context clearly dictates otherwise.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All methods described herein are performed in any suitable order unless otherwise indicated herein or otherwise clearly contradicted by context. In regard to any of the methods provided, the steps of the method may occur simultaneously or sequentially. When the steps of the method occur sequentially, the steps may occur in any order, unless noted otherwise.

In cases in which a method comprises a combination of steps, each and every combination or sub-combination of the steps is encompassed within the scope of the disclosure, unless otherwise noted herein.

Each publication, patent application, patent, and other reference cited herein is incorporated by reference in its entirety to the extent that it is not inconsistent with the present disclosure. Publications disclosed herein are provided solely for their disclosure prior to the filing date of the present invention. Nothing herein is to be construed as an admission that the present invention is not entitled to antedate such publication by virtue of prior invention. Further, the dates of publication provided may be different from the actual publication dates which may need to be independently confirmed.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

Example 1

The disclosed method and system employs an artificial intelligence (AI)/machine learning (ML)-driven technology to measure chronic non-healing wounds automatically, for example, by using a smartphone or desktop computer. The wound data generated provides detailed wound healing trends that facilitate better decision making and proactive wound healing interventions. The system is continuously refined with the machine learning algorithm where over 800 wounds are measured on a daily basis. This is possible with a continuous flow of wound images directly from healthcare providers. The disclosed system is secure and HIPAA compliant.

The disclosed method and system addresses the need for wound care specialists to have a standardized way to treat wounds in a consistent and reliable way. Accurate wound measurements and valid healing trends or vital to improve it informed decision-making and better risk management in this often overlooked area of healthcare. And precise measurement, poor communication and incomplete documentation all lead to increased exposure to adverse adverse consequences for the patient and the organization. Providers are now expected to meet quality indicators associated with hospital quiet pressure ulcers readmissions amputation documentation standard and patient satisfaction.

The disclosed method and system leverages AI/ML for accurate and automatic wound measurement of patients' chronic wounds. It provides wound detection with tissue segmentation. The disclosed method and system also offers a wound dressing algorithm for standardization and regularly leverages Biologics (skin substitutes) to significantly improve patients' wound healing rates.

The disclosed method and system unleashes the full potential of healthcare providers by transforming time-consuming workflows into AI/ML driven processes that have essentially allowed healthcare providers to be "human" again—spending more time being doctors and nurses and less time doing data entry. The AI/ML-driven wound measuring system has allowed for analysis of over 800 wounds daily; a task that typically takes 3-5 days to complete. As a result of this achievement, the healthcare providers are able to complete detailed documentation required by Medicare within only a few minutes, resulting in rapid claims submissions and ultimately predictable robust revenue. Within typical wound care entities, wound treatments can vary from provider to provider, depending on experience and training. However, with the disclosed method and system (e.g., Advanced Wound Care Dressings treatment algorithm), all treatments are standardized based on a number of clinical parameters: (1) wound exudate, (2) wound classification, (3) wound size, and (4) primary dressing selection. The system has also generated valuable "exhaust data," such as (i) the best treatment protocols for certain types of wounds, (ii) primary data for predictive wound healing models, and (iii) refinement in product utilization, warehousing, and fulfillment.

This disclose also provides the following algorithms and workflows (FIGS. 1-4):
1. Biologics graft/skin substitute waste minimization algorithm: this ensures that the wound area vs. graft size/skin substitute maintains the smallest possible waste by employing the most efficient graft size combination. Wastage is a big problem in the medical world and this algorithm manages to achieve that with minimum wastage.
2. Treatment protocol algorithm allows for the use of certain parameters in order to select the correct treatment protocol and plan of care. Parameters used are but not constrained to wound size, wound stage, exudate etc. This promotes advanced wound care dressings standardization enhancing continuity of care.
3. Senaite Lab module workflow.
4. Custom reports running 100% compliance documentation with medicare requirements for DME, Wound debridement and biologics. This mitigates financial claw back due to insufficient reporting. In the long run regulatory oversight is strengthened, and doctors can concentrate on delivering care to the patients.
5. AI-based wound detection and tissue segmentation models that predict accurately to 96% about the length and breadth of wound, and predict the percentage of granulation or fibrous and necrotic tissue without doctor or nurse intervening manually. Thus, the disclosed methods resolve errors in measurement and lack of continuity in care problems.

Biologics OCR

This disclosure provides a process to automate the process to have a solution where once the clinicians upload biologics pdf/image, it should automatically fill PN/SN number and also recommends Size and Units. An example algorithm for the process is provided below:

Algorithm:
1. First it recognizes the grafts using Mask RCNN
2. Then it crops out each Graft
3. Process each Graft using OCR
4. Extract the SN/PN number per Graft.

Codes:
{
 "status"
 : true,
 "messa
 ge": "",
 "data":
 {
  "graft ocr": [
   {
    "product_ident
    ification":
    {"SN":
    "RTX230542-
    020 ",
    "PN": "ZNG-020408"
    }
   }
  ]
  "total_grafts
  ":
  {"total_gr
  afts": 1
  }
 }
}

Referral Form OCR

This disclosure provides a solution where once referral form is uploaded in RITA app, it should automatically fill all the fields.

Algorithm:
Textract as OCR was used to process input PDFs/images, and multiple post-processing is performed after this.

| Codes: |
|---|

```
1    {
2         "status": true,
3         "message", "",
4         "data": {
5         "dump": {
6         "Gender ": "Female ",
7         "Date of Birth (Age) ": "10/24/1942 (78) ",
8         "Address ": "3142 E Acoma Dr (Arizona Sun AL) PHOENIX AZ 85032 ",
9         "Triage Code ": "2 ",
10        "Referral Date ": "08/30/2021 ",
35   },
"Phone ": "(480) 329-6085 ", "SSN ": "",
"Frequencies: ": "SN: 1w1, 3w8, . PT: To eval and treat, . OT: To Eval and Treat, ",
"Relationship ": "",
"Primary Clinician ": "TERESA ARAGON Intake ", "NPI": "1609205350 ",
"Case Manager ": "MAYRA CASTANEDA ",
"State ID ": "Not Entered ", "Facsimile ": "(602) 962-5788 ",
"Secondary Insurance ": "",
"Primary Insurance ": "MEDICARE- NGS ", "Medicaid # ": "",
"Primary Aide ": "", "Tertiary Insurance ": "", "Phone: ": "Not Entered ",
"Medicare # ": "3TV5EP7CP95 ",
"Current Episode: ": "08/31/2021 - 10/29/2021 ", "Email Address ": "",
```

-continued

| Codes: |
|---|

```
    "Start of Care: ": "08/31/2021 ", "Comments ": "NONE ",
    "Contact ": "",
    "WellSky ID: ": "3379-109-899 ",
    "Grace Home Health Care ": "(480) 497-0302 ", "Primary Physician: ": "Anna Manalo FNP-C "
36    "referral": {
37    "Phone": "(480) 329-6085 ",
38    "DOB": "10/24/1942 (78) ",
39    "email": "",
40    "Gender": "Female ",
41    "SSN". "",
42    "Address": "3142 E Acoma Dr (Arizona Sun AL) PHOENIX AZ 85032 Not Entered "
43    },
44    "table": [
45    {
46    "column": [
47    "Medicare # ",
48    "Medicaid # ",
49    "SSN ",
50    "Date of Birth (Age) ",
51    "Gender "
52    ],
53    "rows": [
54    [ ],
55    [
56    "3TV5EP7CP95 ",
57    "",
58    "",
59    "10/24/1942 (78) ",
60    "Female "
61    ],
62    [ ]
63    ]
64    },
65    {
66    "column": [
67    "Address ",
68    "Phone ",
69                "Facsimile ",
70                "State ID "
71                ],
72                "rows": [
73                [ ],
74                [
75                "1301 E McDowell Rd PHOENIX AZ 85006 ",
76                "(602) 962-0088 ",
77                "(602) 962-5788 ",
78                "Not Entered "
79                ],
80                [ ]
81                ]
82            }
83        ]
84    }
85 }
```

Tissue Segmentation

All the wound have three main types of tissues: (1) Granulation: Majorly reddish in color; (2) Fibrous: Majorly yellowish in color; and (3) Necrotic: Majorly blackish in color. Once a wound is detected in wound detection, how much percentage of each tissue type described above was present in each of the wounds is also determined.

Algorithm:

Mask RCNN detectron2 Pixel Segmentation Model for Tissue Segmentation was trained to conduct tissue segmentation. This trained tissue segmentation as described herein achieved an better than 94% accuracy.

Codes:
```
{
   "status": 200,
   "message": "Wound Detected Successfully! ", "data":
   {
      "wound": {
         "length": 2.59,
         "width": 2.48,
         "area": 6.42,
         "area_actual": 5.01,
         "perimeter_wound": 8.09
      },
      "uploaded_path": "https://woundpro-ds.s3.amazonaws.com/019b92dc-f876-4608-a77b-7cbe290437e2.jpg?AWSAccessKeyId=AKIAQTDA44BQ7QU54KD4&Signature=11CE2%2BUcVgyaNEKSIJg
mL29vn50%3D&Expires=1685707612", "tissue_percentage": {
         "necrotic": 16.92,
         "fibrous": 5.48,
         "granulation": 77.59
      }
   }
}
```

Wound Detection

Clinicians used to measure wounds by measuring tape. As to decrease time of measuring and as it was prone to error, this disclosure provides a solution where wound should be automatically detected and measured automatically via artificial intelligence.

Algorithm:

A Detectron2 Pixel Segmentation model was trained. Once the wound was detected, the perimeter, area, length and width of the wound was also calculated.

Codes:
```
{
    "status": 200,
    "message": "Wound Detected Successfully! ", "data": {
        "wound": {
            "length": 2.59,
            "width": 2.48,
            "area": 6.42,
            "area_actual": 5.01,
            "perimeter_wound": 8.09
        },
        "uploaded_path": "https://woundpro-ds.s3.amazon-aws.com/019b92dc-f876-4608-a77b-7cbe290437e2.jpg?AWSAccessKeyId=AKIAQTDA44BQ7QU54KD4&Signature=11CE%2BUcVgyaNEKSIJg mL29vn50%3D&Expires=1685707612", "tissue_percentage": {
            "necrotic": 16.92,
            "fibrous": 5.48,
            "granulation": 77.59
        }
    }
}
```

Example 2

Objective assessment of wound healing progress is the basis for determining effectiveness of treatment, and is critical in selecting a suitable treatment plan. Few mathematical models in the literature deal with the complications associated with wound healing. Existing methods for assessment of wound status in terms of time are often based on measurements of wound area or wound perimeter. However, use of the existing methods is limited due at least to their low precision and poor performance in predicting wound healing rates.

Compared to the existing methods, the disclosed methods employs a third component for wound closure which is "Depth" to improve the above healing rate. Instead of calculating area as in the existing methods, the disclosed methods involve calculating Volume, based on the following equation:

$$V/P = -D(c)*t + q$$

V/P is plotted over t(time), and D(c) is continuous linear healing rate. Also, t(closure)=q/D(c).

Below is a comparison report fort the results based on calculation on area vs. volume. The comparison contains 4000 unique wound details. The mean difference between actual and predicted days of closure was also calculated. As demonstrated, the methods as disclosed herein based on calculation of volume of the wound has a smaller mean difference than the existing methods based o calculation of are of the wound.

| Hypothesis Testing paired t test | Mean (Average) | Standard Deviation | Mean Difference Between Actual (day) | P Value | Conclusion |
|---|---|---|---|---|---|
| 2d_tclose (day) | 102.55 | 277.79 | 44.325 | P < 0.001 | The mean of the Actual wound duration, 2d, and 3d are statistically significant (p < 0.005) |
| 3d_tclose (day) | 96.938 | 323.90 | 38.715 | P < 0.001 | |
| Actual (day) | 58.233 | 60.442 | — | — | |

As demonstrated, the disclosed methods based on volume measurement can afford higher precision in assessing wound healing rates. The existing methods based on measurements of area of a wound alone are less precise for deeper wounds as it does not account for three-dimensional aspects of wounds. In comparison, would volume measurement as in the disclosed methods are more reflective of the true extent of tissue damage and healing because it accounts for depth of wounds. It is particularly accurate for wounds that have significant depth, like pressure ulcers—a major challenge as our senior population is growing.

Notably, the disclosed methods based on volume measurement provides a comprehensive view of healing, potentially leading to better tailored treatments, and can reveal subtleties in healing progress that area measurement might miss. While volume measurement can require more sophisticated technology and expertise and can be time-consuming and costly, the disclosed methods address these challenges by providing a novel approach to assess wound healing rates by volume measurement based on three-dimensional wound information in wound images automatically extracted by machine learning models.

The present disclosure is not to be limited in scope by the specific embodiments described herein. Indeed, various modifications of the invention, in addition to those described herein, will become apparent to those skilled in the art from the foregoing description and the accompanying figures. Such modifications are intended to fall within the scope of the appended claims.

What is claimed is:

1. A method of determining a wound healing rate of a wound or a portion thereof on a subject, comprising:
    obtaining image data comprising an image of a wound or a portion thereof of a subject;
    automatically segmenting the image into a plurality of regions by a first trained model;

automatically determining a boundary of a wound area of the wound or portion thereof by a second trained model based on the plurality of regions from segmentation;

determining three-dimensional characteristics of the wound area comprising a length, a width, and a depth of the wound or portion thereof;

determining a wound healing rate of the wound based on the three-dimensional characteristics of the wound area and using the equation:

$$V/P = -D(c)*t + q,$$

where V is a volume of wound, P is a perimeter of wound, Dc is a continuous linear healing rate, t is time in between evaluation, and q is time of closure;

predicting an area reduction of the wound or a portion thereof over a predetermined time period; and determining an actual amount of area reduction of the wound or portion thereof over the predetermined time period.

2. The method of claim 1, comprising determining the wound healing rate over the predetermined time period.

3. The method of claim 2, comprising selecting, prior to an end of the predetermined time period, between a standard wound care therapy and an advanced wound care therapy based at least in part on the wound healing rate.

4. The method of claim 1, comprising determining the wound healing rate after the predetermined time period has lapsed.

5. The method of claim 1, wherein the step of predicting an area reduction of the wound or a portion thereof over the predetermined time period is performed by a third trained model.

6. The method of claim 5, wherein the first trained model, the second trained model, or the third trained model comprises one or more machine learning models.

7. The method of claim 6, wherein the one or more machine learning models comprise a classifier.

8. The method of claim 6, wherein the one or more machine learning models comprise a neural network, a convolutional neural network (CNN), a deep convolutional neural network (DCNN), a cascaded deep convolutional neural network, a simplified CNN, a shallow CNN, or a combination thereof.

9. The method of claim 6, wherein the one or more machine learning models are trained using a wound, burn, or ulcer image set.

10. The method of claim 1, comprising updating the third trained model with new training data comprising at least the image of the wound or portion thereof and the actual amount of area reduction of the wound or portion thereof.

11. The method of claim 1, comprising determining an expected time period needed for the wound or portion thereof to heal.

12. The method of claim 11, comprising determining the wound healing rate after the expected time period needed for the wound or portion thereof to heal.

13. The method of claim 1, comprising comparing a historical wound healing rate and the wound healing rate.

14. The method of claim 1, wherein the three-dimensional characteristics of the wound area comprise topology information of the wound area.

15. The method of claim 1, wherein the wound is caused by injury, skin lesion, and/or tissue abnormality.

16. The method of claim 1, comprising identifying the wound or portion thereof as granulation, slough, or eschar tissue.

17. The method of claim 1, wherein the image data is acquired from an imaging device comprising one or more imaging sensors.

18. The method of claim 17, wherein the imaging device is contained in a mobile device.

19. A system for determining a wound healing rate of a wound or a portion thereof on a subject, comprising one or more processors configured to implement the method of claim 1.

* * * * *

UNITED STATES PATENT AND TRADEMARK OFFICE
CERTIFICATE OF CORRECTION

PATENT NO. : 12,322,109 B2  
APPLICATION NO. : 18/749457  
DATED : June 3, 2025  
INVENTOR(S) : Bill J. Releford Page 1 of 1

It is certified that error appears in the above-identified patent and that said Letters Patent is hereby corrected as shown below:

In the Specification

Column 3, Line 18 delete "thereof," and insert -- thereof; --.

Column 5, Line 35 delete "thereof," and insert -- thereof; --.

Column 12, Lines 14-15 delete "Deniosing" and insert -- Denoising --.

Column 20, Line 49 delete "adverse adverse" and insert -- adverse --.

Column 24, Line 59 delete "11CE2%" and insert -- 1ICE2% --.

Column 25, Line 40 delete "11CE2%" and insert -- 1ICE2% --.

Column 26, Line 13 delete "based o" and insert -- based on --.

Column 26, Line 14 delete "are" and insert -- area --.

Column 26, Line 35 delete "would" and insert -- wound --.

In the Claims

Column 27, Line 6 in Claim 1, delete "thereof," and insert -- thereof; --.

Signed and Sealed this  
Twenty-third Day of September, 2025

John A. Squires  
*Director of the United States Patent and Trademark Office*